(12) United States Patent  
Rogers et al.

(10) Patent No.: US 6,506,199 B2  
(45) Date of Patent: Jan. 14, 2003

(54) DURA GUARD FOR USE WITH A CRANIOTOME AND METHOD OF USE

(75) Inventors: Laurel Rogers, N. Attleboro, MA (US); Ron Lancaster, Portage, MI (US)

(73) Assignee: Codman & Shurtleff, Inc., Raynham, MA (US)

( * ) Notice: Subject to any disclaimer, the term of this patent is extended or adjusted under 35 U.S.C. 154(b) by 68 days.

(21) Appl. No.: 09/823,693

(22) Filed: Mar. 30, 2001

(65) Prior Publication Data

US 2002/0143356 A1 Oct. 3, 2002

(51) Int. Cl.$^7$ ............................................. A61B 17/14
(52) U.S. Cl. ........................................ 606/172; 606/176
(58) Field of Search ..................... 606/172, 176–179, 606/79, 80, 82; 128/898

(56) References Cited

U.S. PATENT DOCUMENTS

| | | | |
|---|---|---|---|
| 2,698,621 A | | 1/1955 | Fernandez |
| 3,308,828 A | | 3/1967 | Pippin |
| 4,071,030 A | * | 1/1978 | Hedrick ........................ 606/172 |
| 4,340,060 A | | 7/1982 | Berke et al. |
| 5,304,191 A | * | 4/1994 | Gosselin ....................... 606/172 |
| 5,628,748 A | | 5/1997 | Vicari |
| 6,001,115 A | * | 12/1999 | Ahola et al. .................. 606/176 |

* cited by examiner

*Primary Examiner*—Gloria M. Hale
(74) *Attorney, Agent, or Firm*—Nutter McClennen & Fish LLP (57) ABSTRACT

A guard device with angled cranium guide that can be removably and replaceably attached to an existing craniotome for producing a stable bone flap system includes an elongate stem defining a longitudinal axis between a proximal end and distal end. The proximal end is adapted for attachment to the craniotome. A footplate extends from the distal end of the stem at an angle with respect to the longitudinal axis of the stem. The footplate is positioned adjacent to the cutting portion of the craniotome and prevents the cutting portion from penetrating too far into the skull. On one side of the stem between the proximal and distal ends is an angled cranium guide. The dura guard with its angled cranium guide enables the surgeon to rest the guide agains the cranium and the maintain the craniotome at a fixed angle to cut a bone flap at an angle.

19 Claims, 8 Drawing Sheets

DURA GUARD FOR USE WITH A CRANIOTOME AND METHOD OF USE

CROSS-REFERENCE TO RELATED APPLICATIONS

Not applicable.

STATEMENT REGARDING FEDERALLY SPONSORED RESEARCH

Not Applicable.

FIELD OF THE INVENTION

The invention relates generally to surgical devices for dissecting bone and tissue, and to methods pertaining thereto. More particularly, this invention relates to a surgical cutting instrument useful in performing craniotomies, and a footed attachment for such an instrument.

BACKGROUND OF THE INVENTION

A craniotomy involves the surgical removal of a section of bone from the skull for the purpose of operating on the underlying tissues, usually the brain. When the surgeon has completed the surgery to the target tissue, the removed section of bone, called the bone flap, is replaced and the skull is allowed to heal.

A craniotomy may be required in cases of trauma, infection, and tumor growth within the skull. Some of the abnormalities that may require a craniotomy include various lesions affecting the skull and brain. Examples of these lesions include: benign tumors of the skull; tumors of the gliomas, the supporting cells of the brain; cancers from other organs that have metastasized to the brain; abscesses, or localized infections; and, meningiomas, benign tumors of the meninges that, if allowed to grow, may compress the brain and cause damage. Other abnormalities may include aneurysms that can rupture and cause hemorrhaging around the brain, and arteriovenous malformations, such as abnormal tangling of the arteries and veins that may bleed and cause a clot within the brain. Patients with high blood pressure may be at risk of rupturing a blood vessel within the brain, resulting in intracerebral hematoma. Another abnormality includes hydrocephalus, which can result from obstruction to the flow of cerebrospinal fluid that bathes the brain. Patients suffering from any of these skull and brain abnormalities may require a craniotomy to treat or remove the affected area.

Surgical cutting instruments, called craniotomes, have been employed for performing these cranial surgeries. Craniotomes typically have a rotating blade or burr at one end and a handle or grip at the opposite end. Most of these cutting tools also have a guard attached to the cutting end to prevent the instrument from penetrating too far into the skull and damaging the underlying membranes.

The procedure for removing the bone flap involves drilling a series of small holes, called burr holes or pilot holes, in the skull. Usually, three holes are drilled at an angle perpendicular to the surface of the cranium. The holes are positioned around the periphery of the proposed bone flap. A craniotome is then used to cut the bone between each adjacent hole in a progressive manner until the bone flap is separated from the surrounding skull. The guard attached to the craniotome prevents the rotating saw from penetrating the dura, the membrane protecting the brain, into the brain itself, which could lead to severe damage. After the bone flap is removed, the surgeon can access the specific lesion or abnormality that is found and perform the necessary surgery. When the surgery is complete, the bone flap is replaced and anchored to the skull with wire sutures, titanium plates and screws, or adhesives. Small titanium plates are used to cover the pilot holes, and the skull is allowed to heal.

Alternatively, titanium plates can be attached to the bone flap before its removal from the skull. After the step of drilling the pilot holes, small titanium plates having multiple screw holes can be attached to the bone flap near these pilot holes. The plate can be attached to the bone flap with a single screw. A plurality of plates can be attached to the bone flap, whereby each plate is attached to the bone flap so as to cover a pilot hole bordering the flap.

To release the bone flap for access to the underlying tissue, the surgeon maneuvers the plates away from the cutting line while using the craniotome to cut between the pilot holes. The plates attached to the bone flap can prevent the flap from falling into the void. When the intracranial procedure is done, the bone flap can be replaced and the titanium plates reoriented to cover the pilot holes. The remaining screw holes of the plates are then screwed in to provide anchorage and rigid fixation of the bone flap to the skull.

In these standard craniotomy procedures, heavy reliance is placed on the fixation system to hold the bone flap in place until natural healing of the bone occurs. is Since the bone flap and the hole have straight edges, i.e., edges that are perpendicular to the surface of the cranium, the bone flap could potentially fall into the hole or out of the skull when the patient moves. Such a system is inherently unstable and requires the use of external fixation means to keep the bone flap in place. Because external fixation means can often increase the amount of pain and trauma experienced by the patient, prolong the duration of the surgical procedure, lead to unnecessary and avoidable scarring, and inconvenience the patient with time-consuming return visits to the surgeon to have the fixation means removed, there exists a need for an inherently stable system that eliminates the need for, or requires less external fixation means, than what is currently available.

SUMMARY OF THE INVENTION

The present invention overcomes the drawbacks inherent in prior art surgical methods and devices by providing a guard device with an angled cranium guide that can be removably and replaceably attached to an existing craniotome for producing a stable bone flap system. The dura guard includes an elongate stem defining a longitudinal axis between a proximal end and a distal end. At the proximal end of the stem the dura guard is adapted for attachment to the craniotome. A footplate extends from the distal end of the stem at an angle with respect to the longitudinal axis of the stem. The footplate is positioned adjacent to, but spaced apart from, the cutting portion of the craniotome and prevents the cutting portion from penetrating too far into the skull, potentially damaging the dura. On one side of the stem, positioned between the proximal and distal ends, is an angled cranium guide that extends from the stem and faces away from the cutting portion of the craniotome. The dura guard with its angled cranium guide enables the surgeon to rest the cranium guide upon the surface of the cranium and maintain the craniotome at a fixed angle while cutting the skull. By holding the craniotome at a steady angle, the surgeon is able to produce a consistent, bevel-edged bone flap and hole having angled edges or walls. The angled edges of the hole in the cranium and the angled edges of the bone flap enable the flap to reattach to the hole in a stable fashion.

In one embodiment of the present invention, the footplate of the dura guard is obtusely angled with respect to its stem. The angle of the footplate with respect to the stem can be set at the same as the angle of the cranium guide to the stem. In an alternative embodiment, the footplate can extend at a different angle than the cranium guide. For example, the footplate can extend perpendicular to the stem. In yet another embodiment, the stem extends parallel to the cutting portion of the craniotome, but could also extend at an angle to the cutting portion.

The present invention also encompasses a method for using a craniotome with a dura guard having an angled cranium guide. The method comprises the steps of providing a craniotome having attached thereto a dura guard with an angled cranium guide, resting the cranium guide against the surface of the skull, guiding the craniotome forward at a fixed angle along the bone surface, and creating an angled cut so as to produce a bevel-cut bone flap. The bone flap is replaced after cranial surgery, and allowed to heal. Fixation systems known in the art such as titanium plates and screws, wire sutures, or adhesives can optionally be used to anchor the bone flap to the skull.

Further features of the invention, its nature and various advantages, will be more apparent from the accompanying drawings and the following detailed description of the drawings and the preferred embodiments.

DETAILED DESCRIPTION OF THE INVENTION

Figure 1:
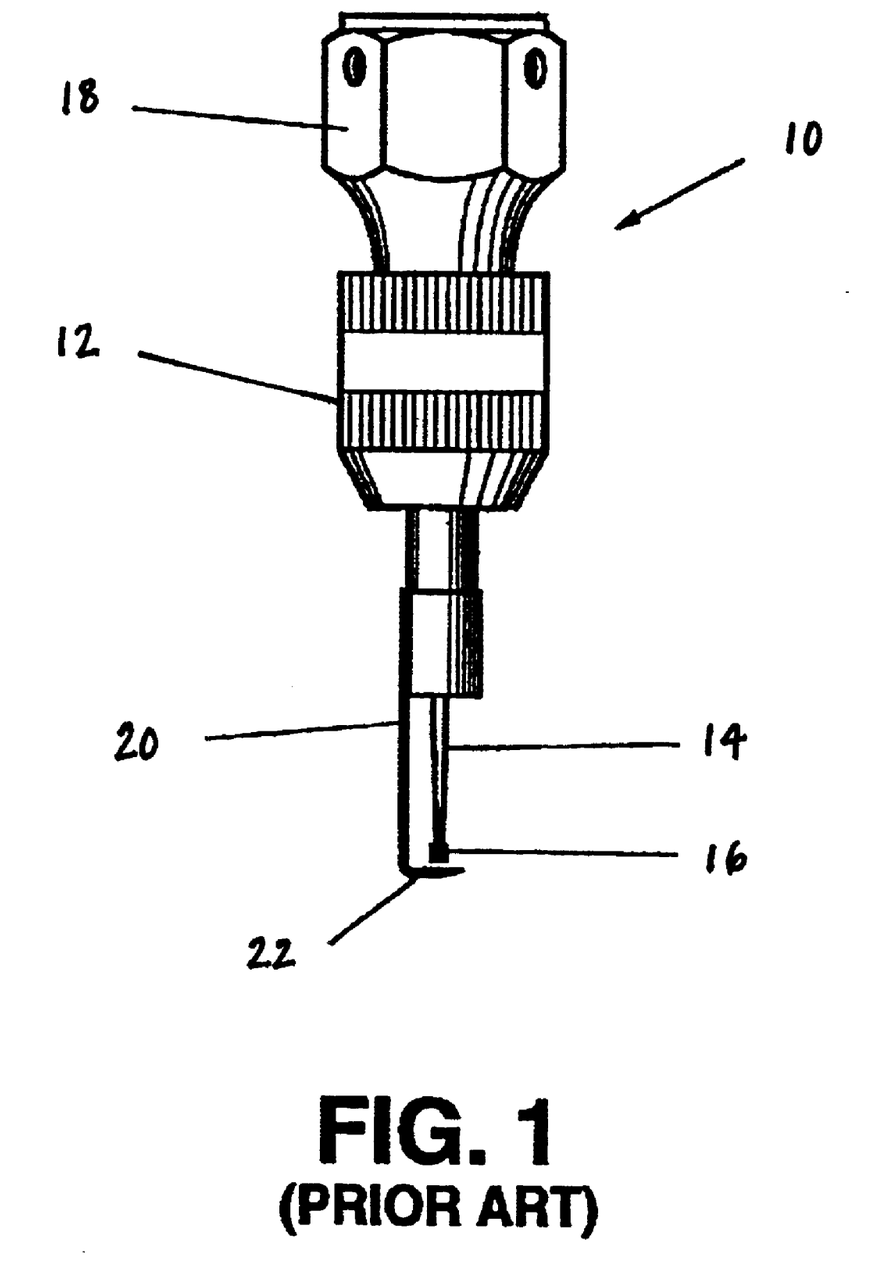
FIG. 1 is a perspective view of a prior art craniotome.

Referring now to the drawings and particularly to FIG. 1, a prior art surgical instrument 10 for dissecting bone is shown. The instrument 10 comprises a housing 12 enclosing a motor for driving a drive shaft. The drive shaft powers a cutting portion, or rotating burr 14, extending from one end of the housing 12. Connected to the housing 12 at an opposite end is a gripping portion 18. During surgery, the operator can manipulate the instrument 10 using the gripping portion 18. Also attached to the housing 12 is a guard 20 having a laterally extending foot 22. The foot 22 prevents the tip 16 of the cutting portion 14 from penetrating too deeply into the skull and damaging the underlying membrane beneath the bone.

During a craniotomy, instrument 10 is used to dissect a bone flap 34 out of the cranium 30. The procedure typically involves drilling a series of small holes, called burr holes or pilot holes, in the skull. Usually, three holes are drilled at an angle perpendicular to the surface of the cranium. The holes are positioned around the periphery of the proposed bone flap 34. The surgeon then uses cutting instrument 10 to cut the bone between each adjacent hole in a progressive manner until the bone flap 34 is separated from the surrounding skull 30. The guard 20 and foot 22 prevent the cutting portion 14 of the instrument 10 from penetrating the dura, the membrane protecting the brain, into the brain itself, which could lead to severe damage. After the bone flap 34 is removed, the surgeon can access the specific lesion or abnormality that is found and perform the necessary surgery. When the surgery is complete, the bone flap 34 is replaced and anchored to the skull with external fixation means 36 such as wire sutures, titanium plates and screws, or adhesives. Small titanium plates are used to cover the pilot holes, and the skull is allowed to heal.

Figure 2:
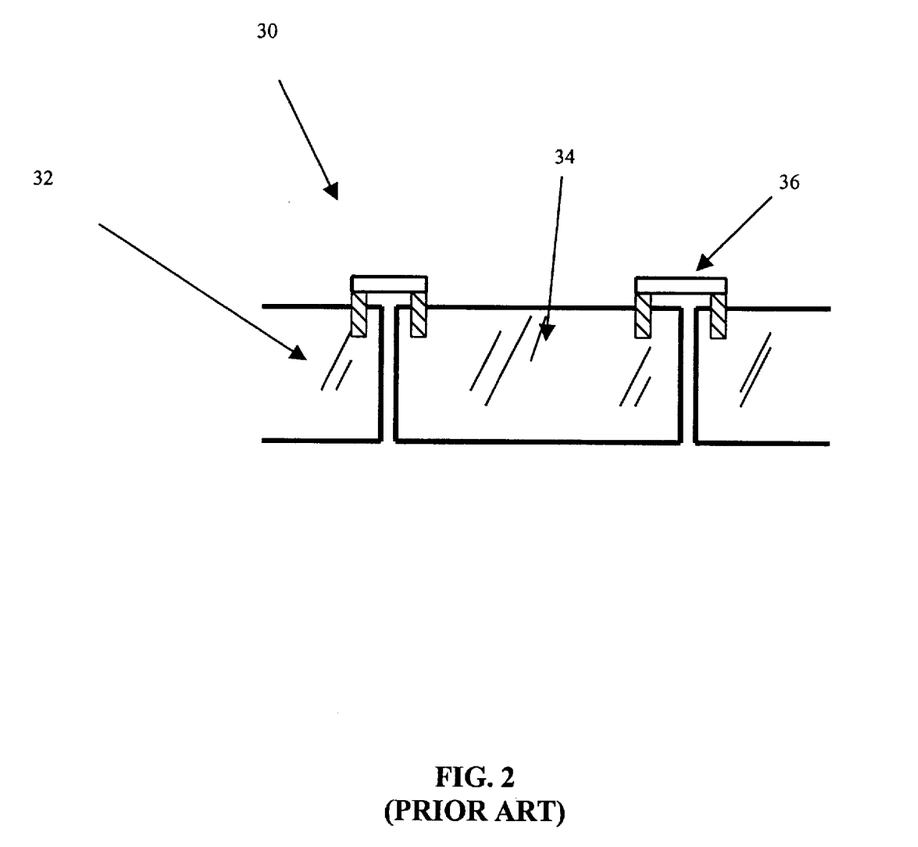
FIG. 2 is a cross-section of a bone flap created using the prior art craniotome of FIG. 1.

As shown in FIG. 2, this procedure results in an inherently unstable system where the bone flap 34 relies on external fixation means 36 to maintain its position within the hole in the cranium 30. Since the bone flap 34 has edges 32 that are cut normal to the surface of the cranium 30, without the external fixation means 36, the bone flap 34 could potentially fall through the hole in the cranium 30, or out of the cranium 30 when the patient moves.

While this bone flap system is acceptable in some situations, there is a need for an improved system that reduces the trauma associated with utilizing external fixation means 36 on a patient. For example, a system that eliminates the necessity for, or reduces the number of, external fixation means 36 required to replace a bone flap 34 could reduce the surgical time needed to complete the surgery. Furthermore, fewer or no fixation means 36 results in less pain and trauma suffered by the patient. The patient could also avoid additional and unnecessary scarring from the fixation means. Finally, the patient could avoid the inconvenient and time-consuming return visits to the hospital to have the fixation means removed after healing is complete.

Figure 3:
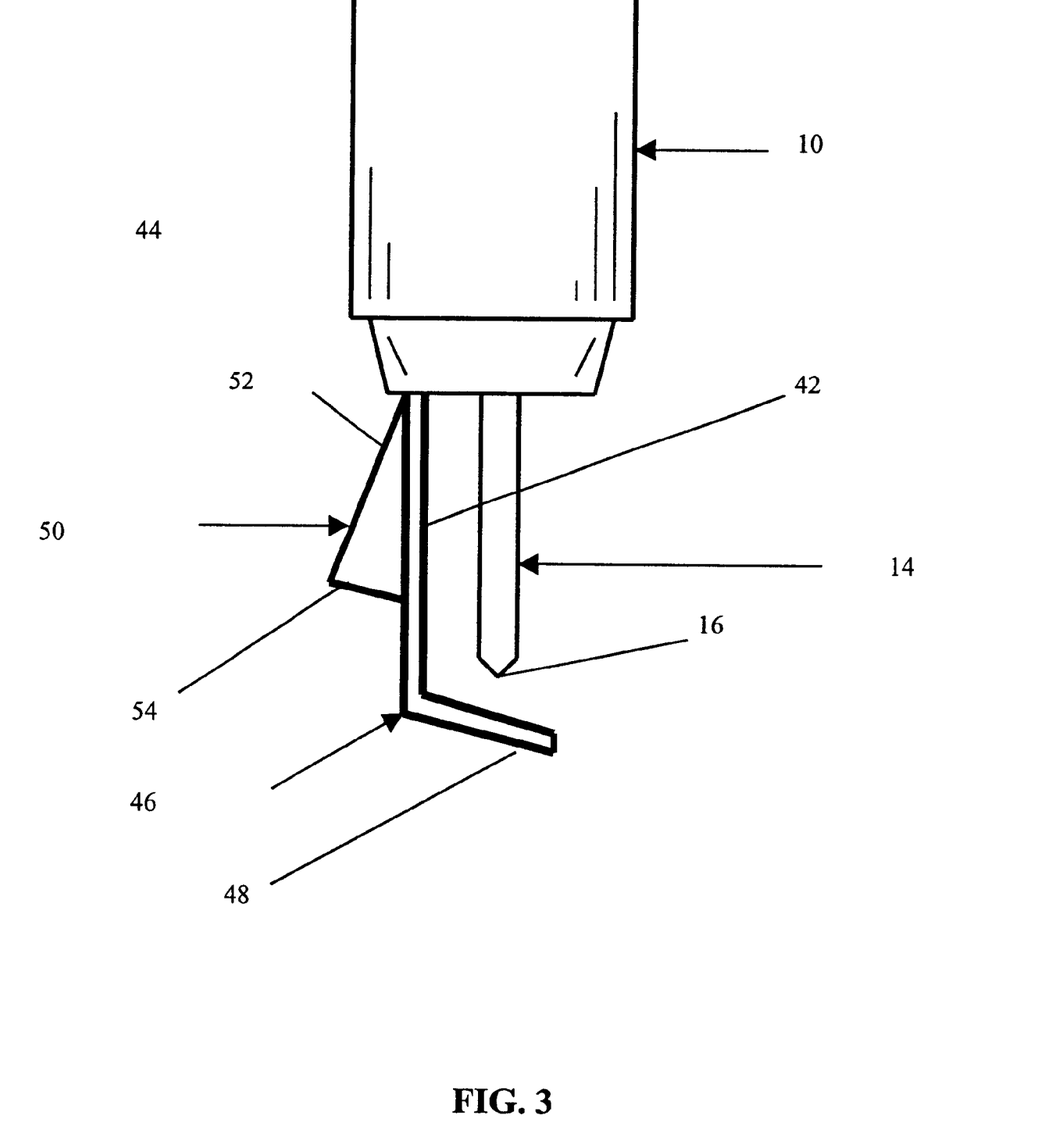
FIG. 3 is a perspective view of a craniotome and a dura guard with a cranium guide of the present invention.

The present invention shown in FIG. 3 contemplates an improved guard 40 that is adapted to be attached to a surgical cutting tool 10, or craniotome, such as the one shown in FIG. 1. The dura guard 40 has a stem 42 that defines a proximal end 44, a distal end 46, and a longitudinal axis extending therebetween. In a preferred embodiment, the stem 42 is positioned parallel to the cutting portion 14 of the craniotome 10. However, it is contemplated that the stem 42 can be angled with respect to the cutting portion 14 as well.

Extending laterally from the distal end 46 of the stem 42 is a footplate 48. When the dura guard 40 is attached to the craniotome 10, the footplate 48 is adapted to be positioned adjacent to and spaced apart from the cutting portion 14 of the craniotome 10. As shown in FIG. 3, the footplate 48 is positioned underneath the cutting portion 14 and is long enough to extend laterally beyond the tip 16 of cutting portion 14. The footplate 48 is effective to prevent the cutting portion 14 of the craniotome 10 from penetrating through the dura of a patient during surgery. In a preferred embodiment, the footplate 48 extends at an obtuse angle with respect to the stem 42.

While footplate 48 is illustrated as having flat inner and outer surfaces, it is contemplated that footplate 48 could also encompass other shapes. For example, footplate 48 could have a curved tip, or J-shape. Alternatively, footplate 48 could also have contoured surfaces. Footplate 48 could have a concave inner surface, and a convex outer surface that would make it cup-shaped.

The dura guard 40 also includes a cranium guide 50 extending from the stem 42 in an opposite direction from the footplate 48. The cranium guide 50 is shaped like a triangular protrusion, with one side of the triangle being the stem 42. A second side 52 of the protrusion extends away from the stem 42 and cutting portion 14 in a direction opposite to the footplate 48. A third side, or base 54, connects the second side 52 to the stem 42 and is shown as the bottom of the protrusion in FIG. 3. In one embodiment, the triangle formed by guide 50 is a right triangle, with the angle formed by second side 52 and base 54 being a right angle. The base 54 is angled with respect to the stem 42 and is adapted to seat against a cranium during surgery. In a preferred embodiment, the angle ($\alpha$) formed by the stem 42 and the base 54 is an obtuse angle. The angle a may be in the range of about 1000° to about 1350°.

While the cranium guide 50 is shown in FIG. 3 as being integral with the stem 42, it is contemplated that the cranium guide 50 could also take other configurations while still providing all the benefits accorded with this invention. For example, the cranium guide 50 can be formed as a separate element from the stem 42. In such an embodiment, the cranium guide 50 could comprise a solid wedge with one side being selectively attachable to the stem 42 of the dura guard 40, with an adjacent side providing the surface upon which the craniotome 10 rests against the cranium. The attachment means could be a snap-fit mating configuration on a side of the cranium guide 50 and stem 42 that would allow easy attachment and removal of the cranium guide 50. This embodiment enables the surgeon the flexibility to control the angle of the dura guard 40 by selectively attaching a particular cranium guide 50 having a corresponding angled base.

Further, it is also not necessary that the cranium guide 50 be solid. In another contemplated embodiment, the cranium guide 50 could comprise an L-shaped wire or series of bent wires having a surface upon which to rest the craniotome 10 against the cranium. The wire or wires could attach to the proximal end 44 of stem 42 and be free from attachment at the opposite end. In this embodiment, the wire or wires could also be formed from a malleable metal to allow the surgeon to manually bend the wire or wires to the specific angle he desires.

The proximal end 44 of dura guard 40 is adapted to be removably and replaceably attached to the craniotome 10. The dura guard 40 can be attached to the craniotome 10 by any conventional means known in the art. Preferably, the dura guard 40 is rotatably attached so that the surgeon can move the dura guard 40 either to the left or right side of the cutting portion 14 as necessary, without having to remove and reattach the dura guard 40 during surgery.

Figure 4:
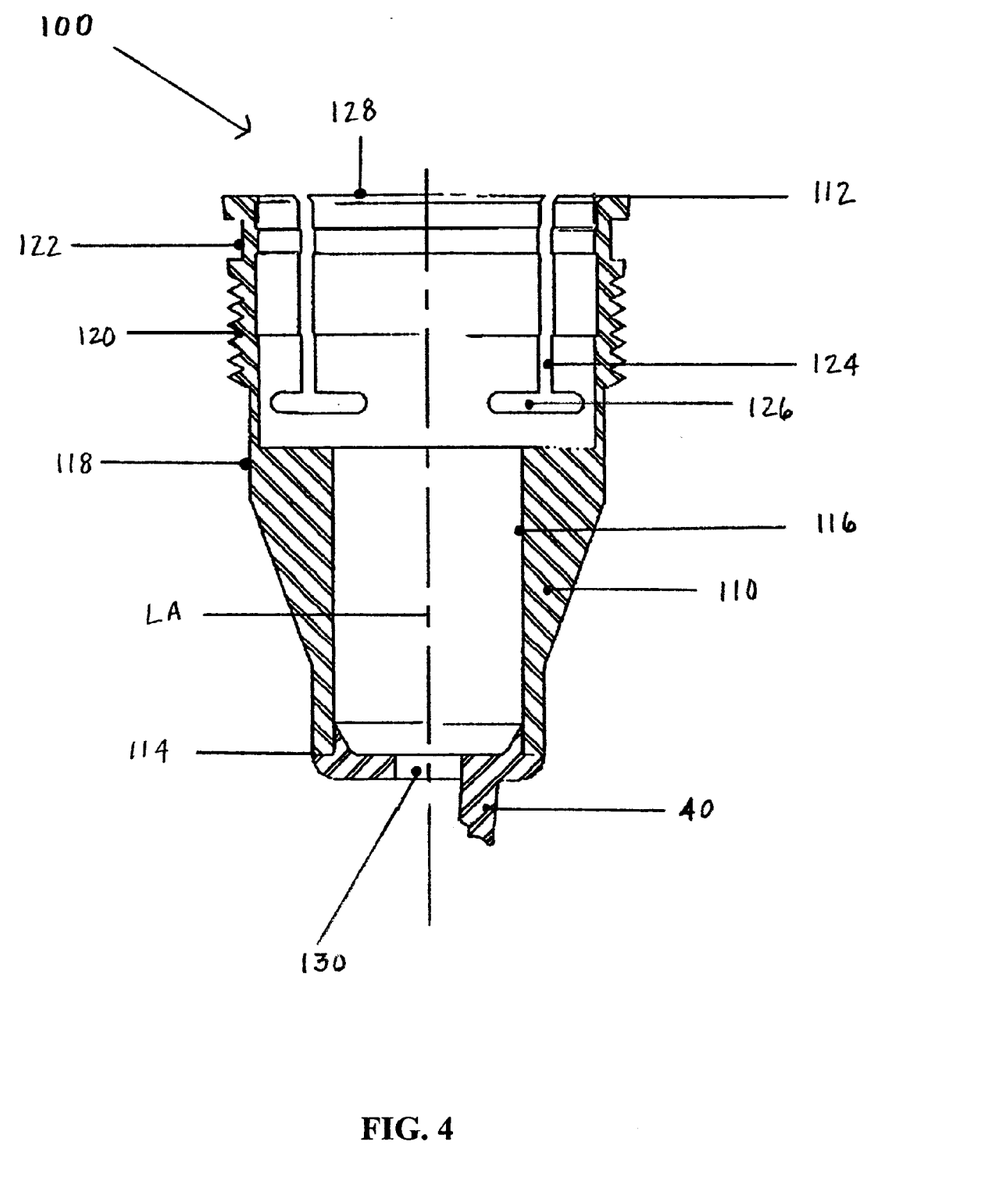
FIG. 4 is a partial cut-away cross-section of an attachment assembly used with the present invention.
Figure 5:
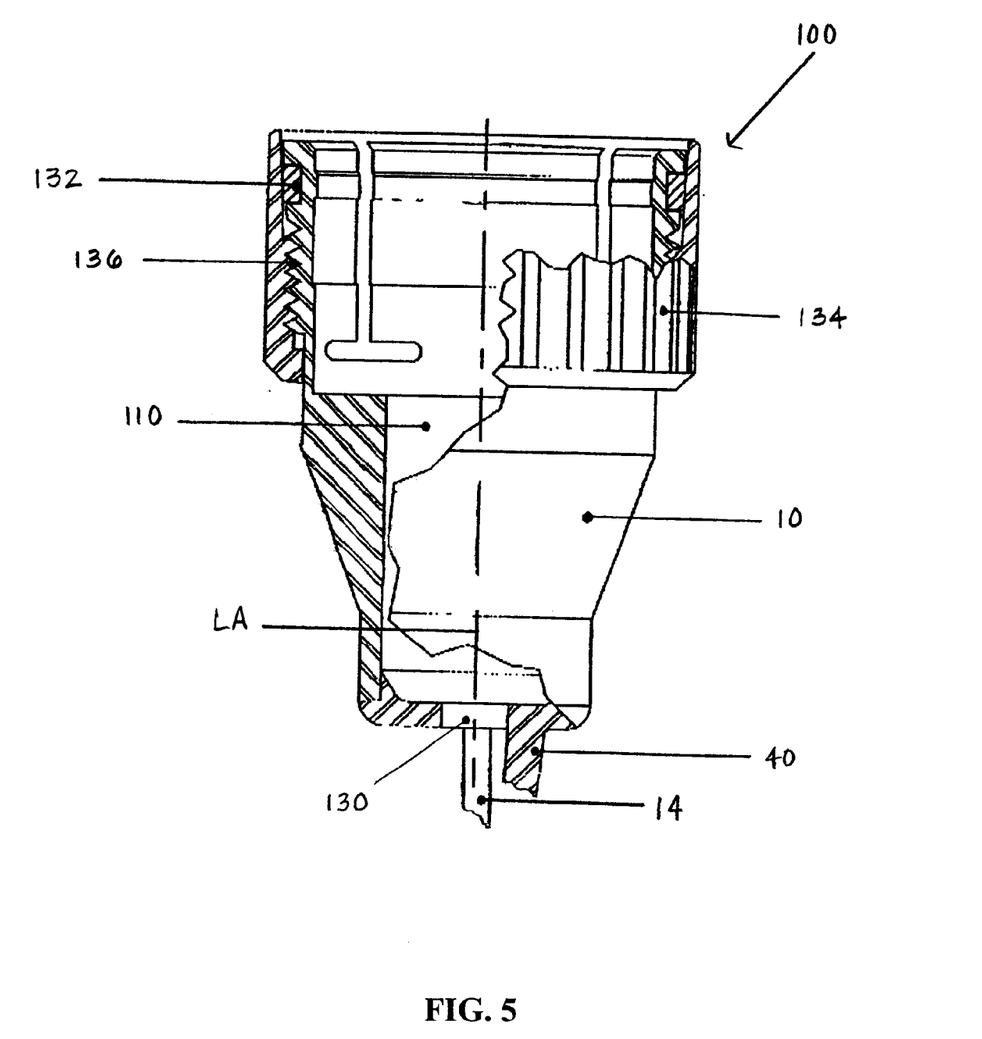
FIG. 5 is a partial cut-away cross-section of the attachment assembly of FIG. 4 with the craniotome of FIG. 1.

FIGS. 4 and 5 illustrate an exemplary embodiment of an attachment assembly 100 for attaching the dura guard 40 to the craniotome 10. As shown in FIG. 4, the attachment assembly 100 includes a sleeve 110 having a proximal end 112 and distal end 114 that is attached to the dura guard 40 of the present invention. The inner surface 116 of the sleeve 110 is configured and dimensioned to accept a standard craniotome 10. The outer surface 118 of sleeve 110 has threads 120 extending around the sleeve 110, near the proximal end 112. Adjacent to the threads 120 is a groove 122 running circumferentially around the proximal end 112. Sleeve 110 also includes longitudinal slits 124 that extend from the proximal end 112 of the sleeve 110, the slits 124 ending in lateral slats 126.

To employ attachment assembly 100, a standard craniotome 10 such as the one depicted in FIG. 1 is introduced into the sleeve 110 at the large opening 128 at the proximal end 112. Sleeve 110 is then slid over the craniotome 10 along longitudinal axis LA, until the cutting portion 14 extends all the way out from small opening 130 at the distal end 114. The craniotome 10 should achieve a snug fit with the inner surface 116 of the sleeve 110, which inner surface 116 is shaped and sized to complement the outer surface of craniotome 10. Once the sleeve 110 is in place, a compression ring 132 as shown in FIG. 5 is inserted into groove 122. Pressure nut 134 having internal threads 136 is then threaded onto proximal end 112 of sleeve 110 and tightened to secure sleeve 110 against craniotome 10.

Attachment assembly 100 enables an operator to easily and quickly rotate the guard 40 about the cutting portion 14, depending on the particular needs of the surgeon. If the surgeon needs to rotate the dura guard 40, he can loosen the nut 134 and rotate the sleeve 110 until the dura guard 40 is properly positioned. When the dura guard is in the desired position, the pressure nut 134 is tightened, and the sleeve 110 is secured against the craniotome 110 once again.

Figure 6:
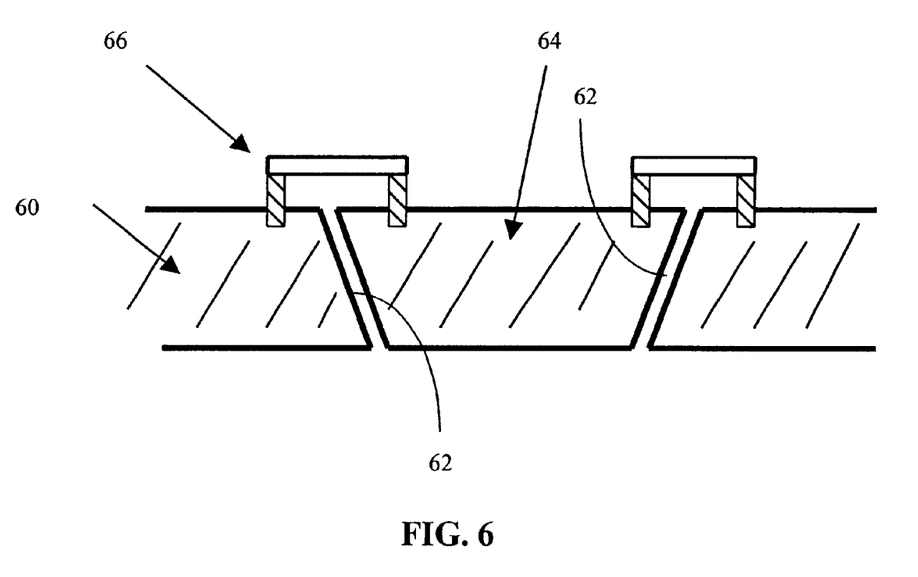
FIG. 6 is a cross-section of a bone flap created using the craniotome and dura guard with cranium guide of FIG. 3.
Figure 7:
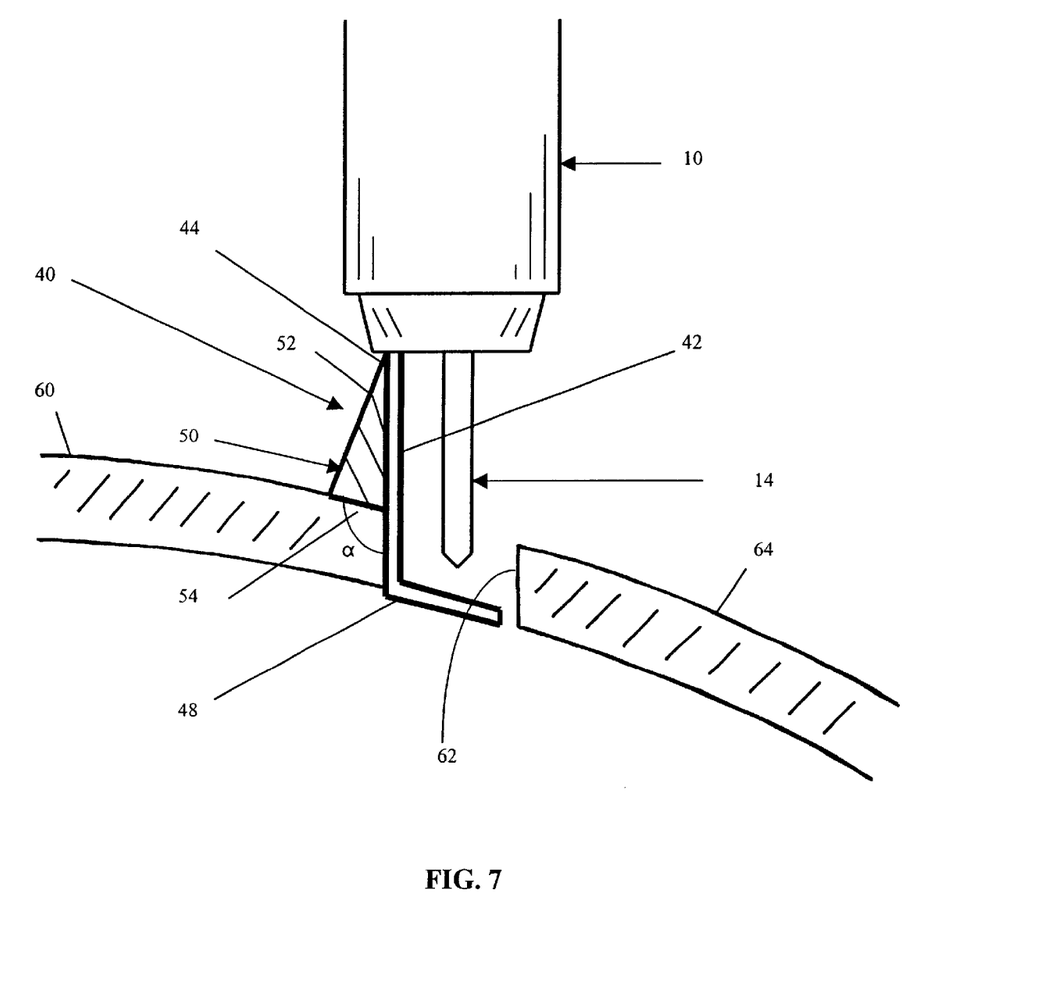
FIG. 7 is a perspective view of the craniotome and dura guard with cranium guide of FIG. 3 in use during a craniotomy.
Figure 8:
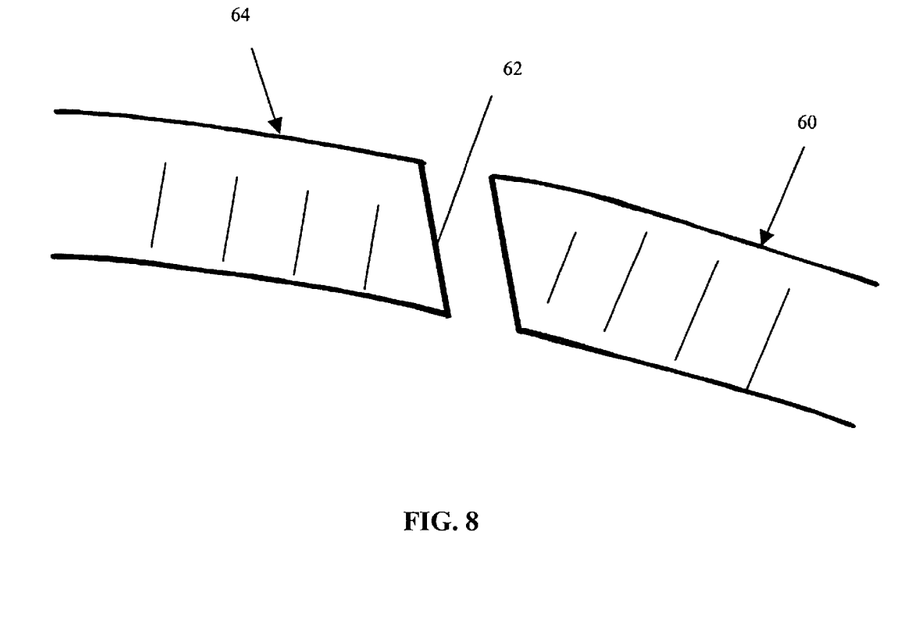
FIG. 8 is an exploded view of the bone flaps of FIGS. 6 and 7.

FIG. 6 illustrates the stable system produced by the improved dura guard 40 of the present invention. After pilot holes are drilled, the craniotome 10 having the improved dura guard 40 attached thereto is placed inside the hole. In FIG. 7, the base 54 of the dura guard 40 rests against the surface of the cranium 60 as the surgeon slides the craniotome 10 forward, creating an angled cut in the cranium 60 as shown in FIGS. 6, 7 and 8. The bone flap 64 that is produced has a beveled edge 62 that, when placed back on the cranium 60, creates the inherently stable system of FIG. 4. The bone flap 64 is able to withstand the external forces against the system and stay within the hole in the cranium 60. External fixation means 66 known in the art such as wire sutures, titanium plates and screws, or adhesives can also be employed, if desired. Small titanium plates can also be used to cover the pilot holes.

The angled cranium guide 50 of the dura guard 40 enables a surgeon to easily and effortlessly produce the stable system illustrated in FIGS. 6, 7 and 8. Using the cranium guide 50, the surgeon can produce a consistent angular cut since the craniotome 10 is held at a fixed angle. Furthermore, the cranium guide 50 allows the surgeon to cut the beveled bone flap quickly. In a preferred embodiment, the angle of the footplate 48 with respect to the stem 42 is identical to the angle of the base 54 to the stem 42. However, the footplate 48 can also extend at a different angle from the stem 42, such as at a perpendicular angle. Irrespective of the angle of the footplate 48, it is important that the thickness of the bone flap remain constant. And, while it is contemplated that the angled base 54 of the dura guard 40 is the primary structure that enables the surgeon to create the angled cut, it is also possible to have the stem 42 angled with respect to the cutting portion 14 of the craniotome 10 to produce this effect.

It will be understood that the foregoing is only illustrative of the principles of the invention, and that various modifications can be made by those skilled in the art without departing from the scope and spirit of the invention. All references cited herein are expressly incorporated by reference in their entirety.

What is claimed is:

1. A guard device for attachment to a craniotome, comprising:

an elongate stem having a proximal end adapted to be removably and replaceably attached to the craniotome, a distal end, and a longitudinal axis therebetween;

a footplate extending from the distal end of the stem, the footplate extending at an angle with respect to the longitudinal axis of the stem; and a cranium guide extending from the stem between the proximal end and distal end of the guard device.

2. The device of claim 1, further being adapted to be rotatably attached to the craniotome.

3. The device of claim 1, wherein the footplate extends at an obtuse angle with respect to the longitudinal axis of the stem.

4. The device of claim 3, wherein the obtuse angle is about 100° to about 135°.

5. The device of claim 1, wherein the footplate is adapted to be positioned adjacent to and spaced axially apart from a cutting portion of the craniotome.

6. The device of claim 5, wherein the footplate is effective to prevent the cutting portion of the craniotome from penetrating through the dura of a patient.

7. The device of claim 1, wherein the cranium guide comprises a triangular protrusion having as a first side a portion extending parallel to the stem, a second side opposite to the first side and extending away from the stem, and a base connecting the first side and second side, the base being angled with respect to the longitudinal axis of the stem.

8. The device of claim 7, wherein the first side is integral with the stem.

9. The device of claim 7, wherein the cranium guide extends away from a cutting portion of the craniotome.

10. The device of claim 7, wherein the angle formed by the footplate and the stem is the same as the angle formed by the base of the cranium guide and the stem.

11. The device of claim 10, wherein the angle is in the range of about 100° to about 135°.

12. The device of claim 7, wherein the angle formed by the base of the cranium guide and the stem is obtuse.

13. The device of claim 12, wherein the angle is in the range of about 100° to about 135°.

14. The device of claim 7, wherein the base of the cranium guide is adapted to seat against a cranium of a patient.

15. The device of claim 1, wherein the longitudinal axis of the stem extends parallel to a cutting portion of the craniotome.

16. A guard device for attachment to a craniotome, comprising:

an elongate stem having a proximal end adapted to be removably and replaceably attached to the craniotome, a distal end, and a longitudinal axis therebetween;

a footplate extending from the distal end of the stem, the footplate extending at an obtuse angle with respect to the longitudinal axis of the stem; and a cranium guide extending from the stem between the proximal end and distal end of the guard device, the cranium guide comprises a triangular protrusion having as a first side a portion extending parallel to the stem, a second side opposite to the first side and extending away from the stem, and a base connecting the first side and second side, the base being angled with respect to the longitudinal axis of the stem;

wherein the angle formed by footplate and the stem is the same as the angle formed by the base of the cranium guide and the stem.

17. The device of claim 16, wherein the angle is in the range of about 100° to about 135°.

18. A surgical system for cutting a bone flap from a cranium, comprising:

a cutting instrument comprising a housing enclosing therein a motor for driving a drive shaft, the drive shaft providing power to a cutting portion extending from one end of the housing, the housing having at an opposite end a griping portion for manipulating the instrument during surgery; and a dura guard comprising an elongate stem having a proximal end adapted to be removably and replaceably attached to the cutting instrument, a distal end, and a longitudinal axis therebetween;

a footplate extending from the distal end of the stem, the footplate extending at an obtuse angle with respect to the longitudinal axis of the stem; and a cranium guide extending from the stem between the proximal end and distal end of the guard device, the cranium guide comprises a triangular protrusion having as a first side a portion extending parallel to the stem, a second side opposite to the first side and extending away from the stem, and a base connecting the first side and second side, the base being angled with respect to the longitudinal axis of the stem;

wherein the angle formed by footplate and the stem is the same as the angle formed by the base of the cranium guide and the stem.

19. A method of cutting a beveled bone flap in a cranium comprising the steps of:

drilling pilot holes around a periphery of the bone flap;

providing a craniotome having attached thereto a guard device comprising:

an elongate stem having a proximal end adapted to be removably and replaceably attached to the craniotome, a distal end, and a longitudinal axis therebetween, a footplate extending from the distal end of the stem, the footplate extending at an angle with respect to the longitudinal axis of the stem, and a cranium guide extending from the stem between the proximal end and distal end of the guard device; resting a base of the cranium guide against the cranium; guiding the craniotome forward at a fixed angle along the surface of the cranium; and cutting the bone flap so as to achieve a beveled edge.

* * * * *